United States Patent
Gao et al.

(10) Patent No.: US 10,886,475 B2
(45) Date of Patent: Jan. 5, 2021

(54) ORGANIC ELECTROLUMINESCENT MATERIALS AND ORGANIC ELECTROLUMINESCENT DEVICES

(71) Applicant: BOE TECHNOLOGY GROUP CO., LTD., Beijing (CN)

(72) Inventors: Xue Gao, Beijing (CN); Fei Liu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 467 days.

(21) Appl. No.: 15/548,880

(22) PCT Filed: Jan. 3, 2017

(86) PCT No.: PCT/CN2017/000013
§ 371 (c)(1),
(2) Date: Aug. 4, 2017

(87) PCT Pub. No.: WO2017/177719
PCT Pub. Date: Oct. 19, 2017

(65) Prior Publication Data
US 2018/0069183 A1 Mar. 8, 2018

(30) Foreign Application Priority Data

Apr. 15, 2016 (CN) .......................... 2016 1 0236613

(51) Int. Cl.
*H01L 51/00* (2006.01)
*C07D 209/82* (2006.01)
(Continued)

(52) U.S. Cl.
CPC ........ *H01L 51/0072* (2013.01); *C07D 209/82* (2013.01); *C07D 241/36* (2013.01);
(Continued)

(58) Field of Classification Search
CPC .. C07D 209/82; C07D 241/36; C07D 251/42; C07F 9/5325; C07F 9/6561; H01L 51/0072
See application file for complete search history.

(56) References Cited

U.S. PATENT DOCUMENTS 8,987,462 B2 3/2015 Kim et al.
2013/0200350 A1 8/2013 Sawada et al.
(Continued)

FOREIGN PATENT DOCUMENTS

CN 103098253 A 5/2013
CN 103214490 A 7/2013
(Continued)

OTHER PUBLICATIONS

Machine translation of JP2015-111624A, 86 pages. (Year: 2015).*
(Continued)

*Primary Examiner* — Matthew E. Hoban
*Assistant Examiner* — Lynne Edmondson
(74) *Attorney, Agent, or Firm* — Dilworth & Barrese, LLP.; Michael J. Musella, Esq.

(57) ABSTRACT

The present disclosure relates to organic electroluminescent materials and organic electroluminescent devices, in particular, discloses a compound of formula (1), wherein $R_1$, $R_2$, $R_3$ and $R_4$ are each independently selected from hydrogen, a substituted or unsubstituted $C_{1-20}$ alkyl, a substituted or unsubstituted $C_{3-20}$ cycloalkyl, a substituted or unsubstituted aromatic hydrocarbyl, or a substituted or unsubstituted aromatic heterocyclic group; and at least one of $R_1$, $R_2$, $R_3$ and $R_4$ contains a group having a hole-transporting ability; and at least one of $R_1$, $R_2$, $R_3$ and $R_4$ contains a group having an electron-transporting ability; A and B each independently represent hydrogen, a substituted or unsubstituted, fused
(Continued)

aromatic ring, or a substituted or unsubstituted, fused heteroaromatic ring containing a heteroatom(s) selected from O, N and S.

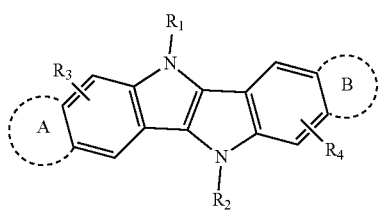

Formula (1)

13 Claims, 1 Drawing Sheet

(51) Int. Cl.
C07D 241/36 (2006.01)
C07D 251/42 (2006.01)
C07F 9/53 (2006.01)
C07F 9/6561 (2006.01)
H01L 51/50 (2006.01)

(52) U.S. Cl.
CPC .......... *C07D 251/42* (2013.01); *C07F 9/5325* (2013.01); *C07F 9/6561* (2013.01); *H01L 51/0085* (2013.01); *H01L 51/5016* (2013.01)

(56) References Cited

U.S. PATENT DOCUMENTS

| 2014/0203257 A1 | 7/2014 | Hwang et al. |
| 2014/0306197 A1 | 10/2014 | Kim et al. |
| 2016/0005979 A1 | 1/2016 | Kim et al. |

FOREIGN PATENT DOCUMENTS

| CN | 103992335 A | 8/2014 | |
| CN | 103098253 B | 9/2015 | |
| CN | 105777809 A | 7/2016 | |
| JP | 2015111624 A | 6/2015 | |
| JP | 2015111624 A * | 6/2015 | ......... H01L 51/0072 |
| KR | 20150030794 A | 3/2015 | |
| WO | 2011132866 A1 | 10/2011 | |
| WO | 2012035934 A1 | 3/2012 | |
| WO | 2012050003 A1 | 4/2012 | |
| WO | 2014058183 A1 | 4/2014 | |
| WO | 2014061960 A1 | 4/2014 | |
| WO | 2015076599 A1 | 5/2015 | |
| WO | 2015099477 A2 | 7/2015 | |
| WO | 2016017514 A1 | 2/2016 | |
| WO | 2016069321 A3 | 5/2016 | |

OTHER PUBLICATIONS

Jeon et al., "Synthesis of fused phenylcarbazole phosphine oxide based high triplet energy host materials", Jul. 14, 2010, Tetrahedron, 66, pp. 7295-7301. (Year: 2010).*
Extended European Search Report issued by the European Patent Office for the corresponding European Patent Application No. 17745642.3 dated Nov. 11, 2019.
Hong Huang et al., Optimizing the Conjugation Between N,N'-Dicarbazolyl-3,5-Benzene and Triphenylphosphine Oxide as Bipolar Hybrids for Highly Efficient Blue and Single Emissive Layer White Phosphorescent OLEDS; Organic Electronics 14, (2013) pp. 2573-2581.
International Search Report dated Apr. 11, 2017.
Search Report issued by the Chinese Patent Office in the priority Chinese application No. 201610236613.4 dated Sep. 28, 2016.
First Office Action issued by the Chinese Patent Office in the priority Chinese application No. 201610236613.4 dated Dec. 1, 2016.
Second Office Action issued by the Chinese Patent Office in the priority Chinese application No. 201610236613.4 dated Mar. 1, 2017.

* cited by examiner

ORGANIC ELECTROLUMINESCENT MATERIALS AND ORGANIC ELECTROLUMINESCENT DEVICES

TECHNICAL FIELD

The present disclosure relates to an organic electroluminescent materials and organic electroluminescent devices.

BACKGROUND

The basic structure of Organic Light-Emitting Diode (OLED) includes an anode layer, a functional layer and a cathode layer. The functional layer includes a hole-transporting layer, a light-emitting layer and an electron-transporting layer. When an appropriate voltage is supplied to a cathode and an anode, electrons and holes are injected from the cathode and the anode into the electron-transporting and hole-transporting layers, respectively, and migrate to the light-emitting layer via the electron-transporting and hole-transporting layers, respectively. Holes and electrons recombine and emit light in the light-emitting layer, thereby realizing light-emitting of the OLED device itself. However, efficiency and life of the OLED needs to be further improved.

SUMMARY

The present disclosure provides a compound of formula (1),

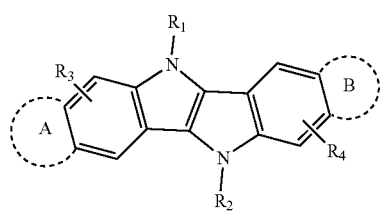

Formula (1)

wherein $R_1$, $R_2$, $R_3$ and $R_4$ are each independently selected from hydrogen, a substituted or unsubstituted $C_{1-20}$ alkyl, a substituted or unsubstituted $C_{3-20}$ cycloalkyl, a substituted or unsubstituted aromatic hydrocarbyl, or a substituted or unsubstituted aromatic heterocyclic group; and at least one of $R_1$, $R_2$, $R_3$ and $R_4$ contains a group having a hole-transporting ability; and at least one of $R_1$, $R_2$, $R_3$ and $R_4$ contains a group having an electron-transporting ability; A and B each independently represent hydrogen, a substituted or unsubstituted, fused aromatic ring, or a substituted or unsubstituted, fused heteroaromatic ring containing a heteroatom(s) selected from O, N and S.

Examples of the present disclosure also provide an organic electroluminescent composition comprising a light-emitting material and a host material, wherein the host material comprises the compound as described above.

Examples of the present disclosure also provide an organic electroluminescent diode device comprising a cathode, an anode and an organic functional layer formed between the cathode and the anode, wherein the organic functional layer comprises at least one light-emitting layer, and the light-emitting layer comprises a light-emitting material and a host material, and wherein the host material comprises the compound as described above.

Examples of the present disclosure also provide a method for the preparation of the above compounds which comprises: forming an indolo[3,2-b]indole main aromatic structure in the compound of formula (1); forming the group having a hole-transporting ability; and forming the group having an electron-transporting ability.

BRIEF DESCRIPTION OF THE DRAWINGS

In order to more clearly illustrate the technical solution of the Examples of the present invention, the drawings of the examples will be briefly described below. It will be apparent that the drawings in the following description are merely illustrative of some examples of the invention and are not intended to limit the invention.

DETAILED DESCRIPTION

Figure 1:
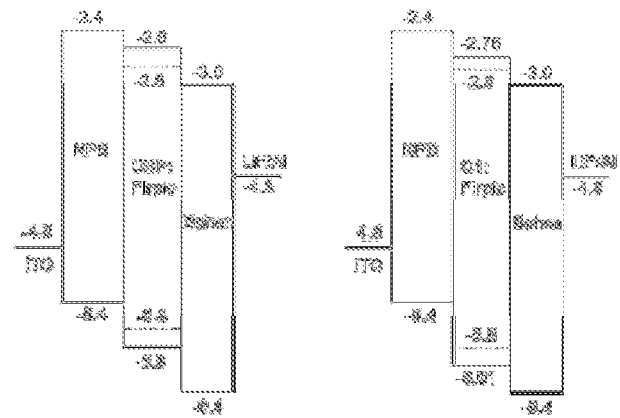
FIG. 1 is a device energy level diagram of the comparative example and working example of the present disclosure.

In order to make purposes, technical solutions and advantages of examples of the present invention more clear, the technical solutions of the examples of the present invention will be described clearly and completely below with reference to the accompanying drawings of the examples of the present invention. Obviously, the described examples are part of the examples of the present invention, not all the examples. Based on the described examples of the present invention, all other examples obtained by one of ordinary skill in the art without creative labor are within the scope of the present invention.

The present disclosure provides a compound of formula (1),

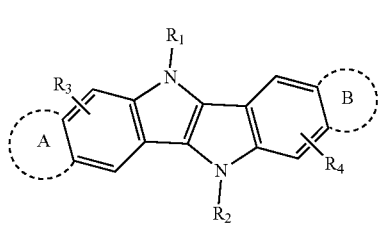

Formula (1)

wherein $R_1$, $R_2$, $R_3$ and $R_4$ are each independently selected from hydrogen, a substituted or unsubstituted $C_{1-20}$ alkyl, a substituted or unsubstituted $C_{3-20}$ cycloalkyl, a substituted or unsubstituted aromatic hydrocarbyl, or a substituted or unsubstituted aromatic heterocyclic group; and at least one of $R_1$, $R_2$, $R_3$ and $R_4$ contains a group having a hole-transporting ability; and at least one of $R_1$, $R_2$, $R_3$ and $R_4$ contains a group having an electron-transporting ability; A and B each independently represent hydrogen, a substituted or unsubstituted, fused aromatic ring, or a substituted or unsubstituted, fused heteroaromatic ring containing a heteroatom(s) selected from O, N and S.

As shown in formula (1), the compound contains an N-containing aromatic group of 5,10-disubstituted indolo[3,2-b]indole. A group having a hole-transporting ability and a group having an electron-transporting ability have been incorporated into a linearly extended i-conjugated system of the compound, so that the compound has both a hole-transporting ability and an electron-transporting ability. When used as a host material in an organic light-emitting material, the compound introduces an O, N, S heteroatom(s) into a linearly extended i-conjugated system, so that the chemical activity of the molecule is effectively reduced while original carrier-transporting properties (i-conjugated system) is maintained, thereby increasing redox stability.

In the present application, "A is a fused aromatic ring" refers to a fused aromatic ring formed by A and a benzene ring to which A is attached. In the present application, "A is a fused heteroaromatic ring" refers to a fused heteroaromatic ring formed by A and a benzene ring to which A is attached. In the present application, "B is a fused aromatic ring" refers to a fused aromatic ring formed by B and a benzene ring to which B is attached. In the present application, "B is a fused heteroaromatic ring" refers to a fused heteroaromatic ring formed by B and a benzene ring to which B is attached.

In some embodiments, the aromatic hydrocarbyl is selected from or includes phenyl, biphenylyl, naphthyl, phenanthryl, naphthylphenyl and fluorenyl, which are substituted or unsubstituted.

In some embodiments, the aromatic heterocyclic group is selected from or includes pyridyl, imidazolyl, carbazolyl and benzimidazolyl, which are substituted or unsubstituted.

In some embodiments, the substituents at each occurrence are independently selected from $C_1$-$C_{10}$ alkyl, $C_1$-$C_{10}$ alkoxyl, $C_3$-$C_{20}$ cycloalkyl, $C_6$-$C_{20}$ aryl or $C_4$-$C_{20}$ heteroaryl.

In some embodiments, the group having a hole-transporting ability is selected from aromatic triamine groups, carbazole groups, organosilicon groups, and organometallic complex groups.

In some embodiments, the group having an electron-transporting ability is selected from groups derived from metal complexes, oxadiazoles, imidazoles, oxazoles, triazoles, benzodiazoles, benzothiadiazoles, pyridines, pyrimidines, pyrazines, quinolines, o-phenanthrolines, quinoxalines, anthrazoles, triazines, organoborons, organosilicons, and diphenylphosphine oxides.

In some embodiments, the group having an electron-transporting ability is a substituted or unsubstituted diphenylphosphine oxide group.

In some embodiments, the group having a hole-transporting ability is a substituted or unsubstituted carbazole group.

In some embodiments, a π-π conjugation is formed between the group having a hole-transporting ability and the indolo[3,2-b]indole main aromatic structure in the compound of formula (1); and a π-π conjugation is formed between the group having an electron-transporting ability and the indolo[3,2-b]indole main aromatic structure in the compound of formula (1). It should be noted that, in general, the group having a hole-transporting ability may be an aromatic group (e.g., comprising an aromatic ring), and thus can form a π-π conjugation with the indolo[3,2-b]indole main aromatic structure upon bonding to the indolo[3,2-b]indole main aromatic structure via a suitable bond (e.g., 6 bond). Similarly, the group having an electron-transporting ability may be an aromatic group (e.g., comprising an aromatic ring), and thus can form a π-π conjugation with the indolo[3,2-b]indole main aromatic structure upon bonding to the indolo[3,2-b]indole main aromatic structure via a suitable bond (e.g., σ bond).

The indolo[3,2-b]indole main aromatic structure described in the present disclosure may refer to the moiety in formula (1) similar to the below formula:

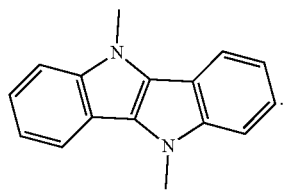 [SMILES: Cn1c2ccccc2c2c1c1ccccc1n2C]

A group with an electron-transporting property (e.g., a diphenylphosphine oxide group) and a group with a hole-transporting property (e.g., a carbazole group) are connected by a linearly extending π-conjugated core (i.e., the indolo [3,2-b]indole main aromatic structure), thereby forming a host material with high thermal stability, chemical stability and bipolar transporting characteristics. The host material can effectively enhance the efficiency and life of OLED when it is used for OLED. Therefore, this material may be used for manufacturing organic electroluminescent devices and also has a wide range of applications in other optoelectronic devices.

The above-mentioned compound containing a group with an electron-transporting property (e.g., diphenylphosphine oxide group) and a group with a hole-transporting property (e.g., a carbazole group) provided in the present application can be used as a host material in an organic electroluminescent layer.

In some embodiments, the compound has at least one of the following structural formulas:

C-1

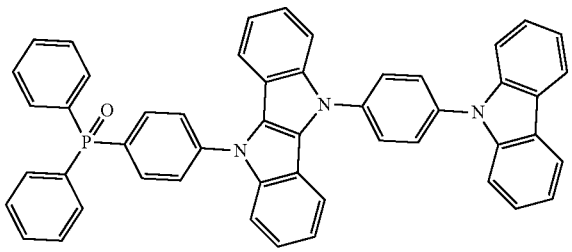

C-2

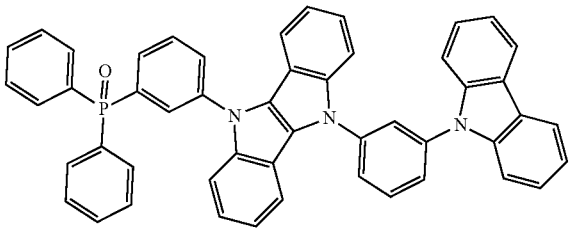

C-3

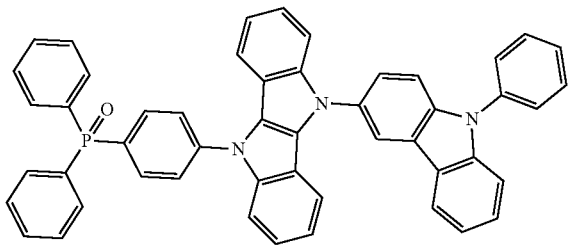

C-4
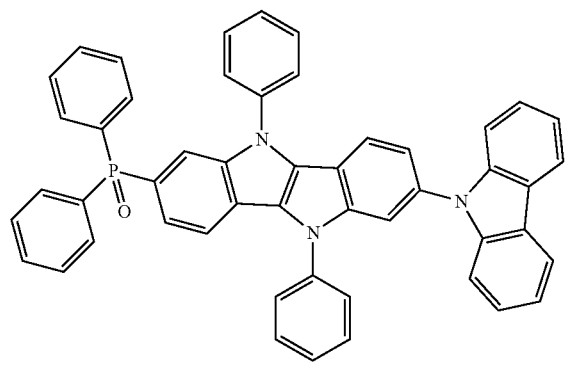
C-5
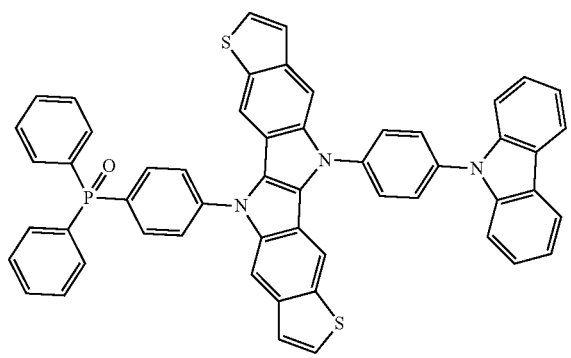
C-6
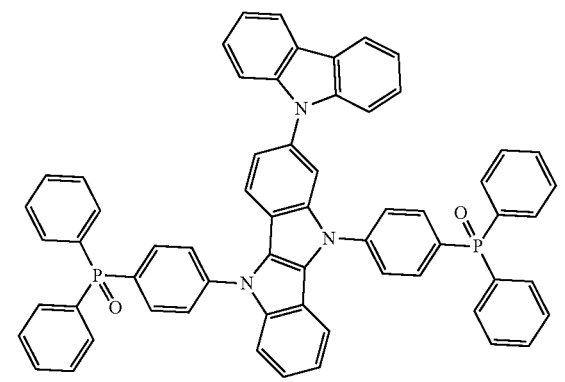
C-7
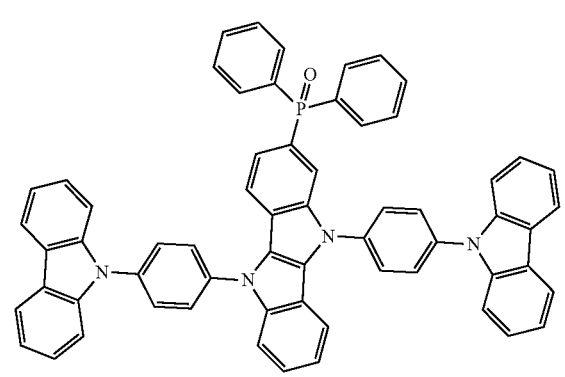
C-8
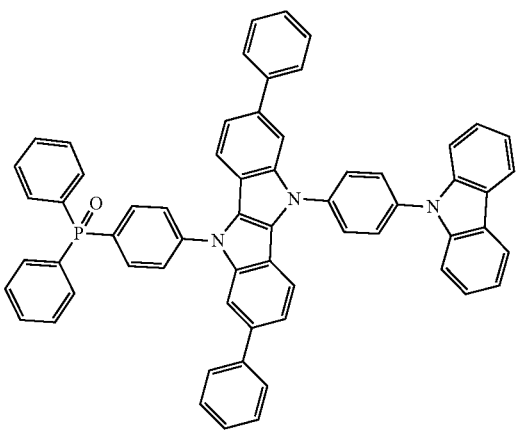
C-9
C-10
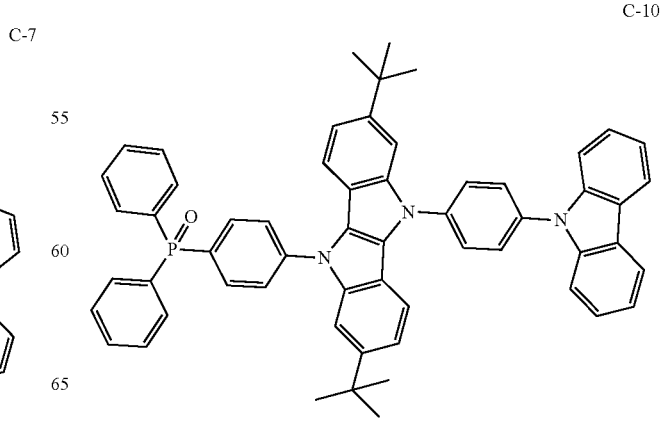

C-11
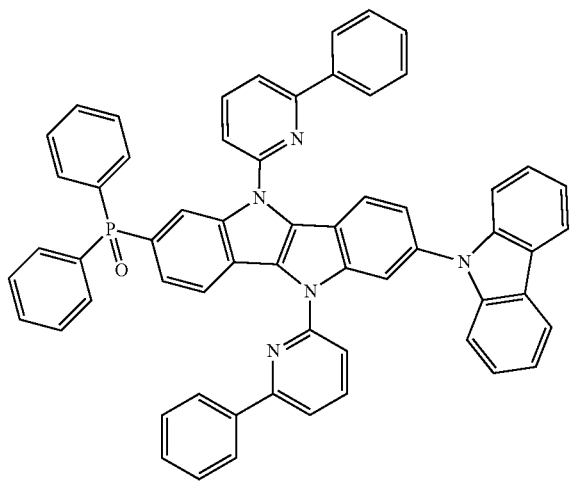
C-12
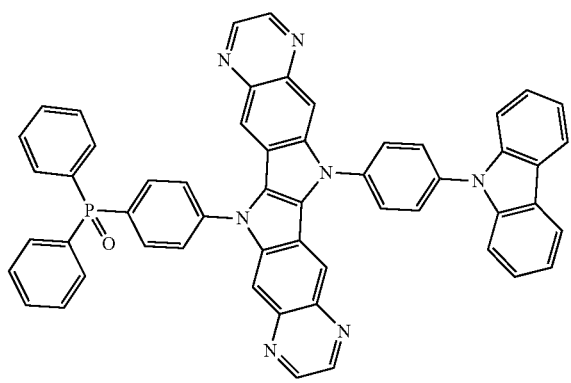
C-13
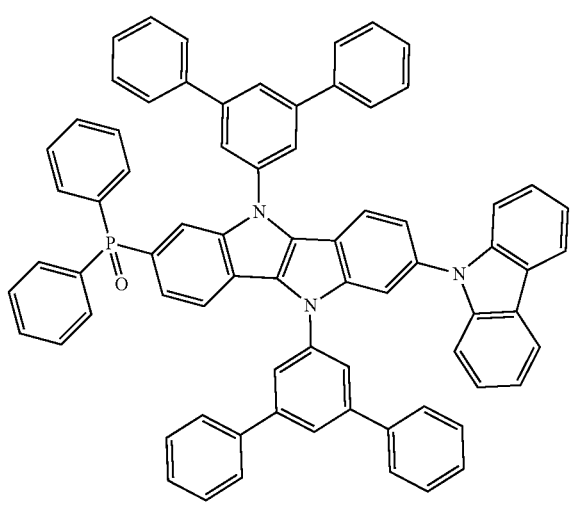
C-14
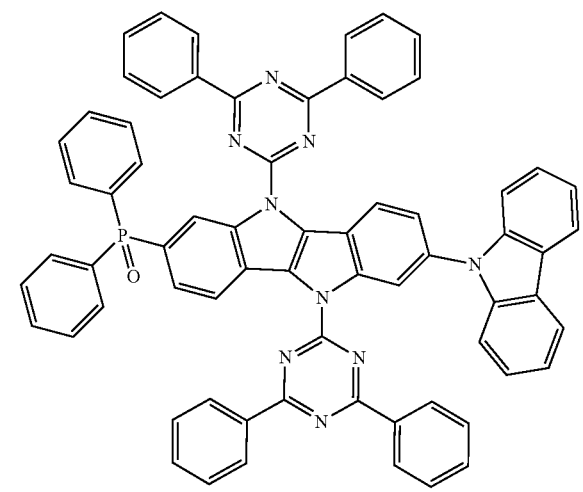
C-15
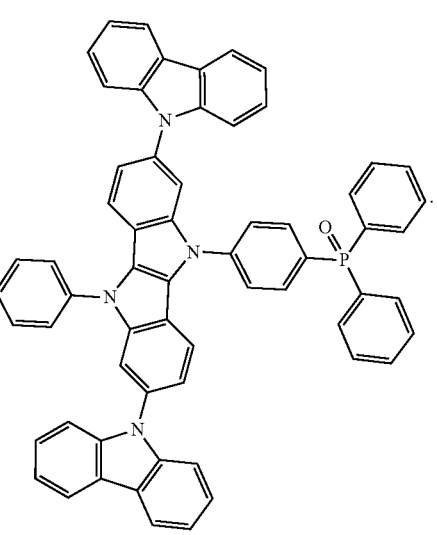
or
C-16
Examples of the present disclosure also provide an organic electroluminescent composition comprising a light-emitting material and a host material, wherein the host material comprises the compound described above.

In some embodiments, the light-emitting material comprises at least one selected from the group consisting of a fluorescent light-emitting material and a phosphorescent light-emitting material.

In some embodiments, the phosphorescent light-emitting material comprises at least one compound selected from the group consisting of Ir complexes, Pt complexes, Os complexes, Ru complexes, Re complexes, and Pd complexes.

In some embodiments, the host material accounts for about 80 to 98 wt %, for example about 85 to 98 wt %, for example about 88 to 97 wt %, for example about 90 to 95 wt %, of the composition. Correspondingly, the light-emitting material accounts for about 2 to 20 wt %, for example about 2 to 15 wt %, for example about 3 to 12 wt %, for example about 5 to 10 wt %, of the composition.

Examples of the present disclosure also provide a method for preparing the compound of formula (1), comprising: forming an indolo[3,2-b]indole main aromatic structure in the compound of formula (1); forming the group having a hole-transporting ability; and forming the group having an electron-transporting ability.

In some embodiments, the group having an electron-transporting ability is a substituted or unsubstituted diphenylphosphine oxide group. The forming of the group having an electron-transporting ability comprises: forming a diphenylphosphine group, and then oxidizing it to form a diphenylphosphine oxide group.

In some embodiments, the group having a hole-transporting ability is a substituted or unsubstituted carbazole group.

In some embodiments, the indolo[3,2-b]indole main aromatic structure is formed by the method represented by any of the following equations (1) to (4):

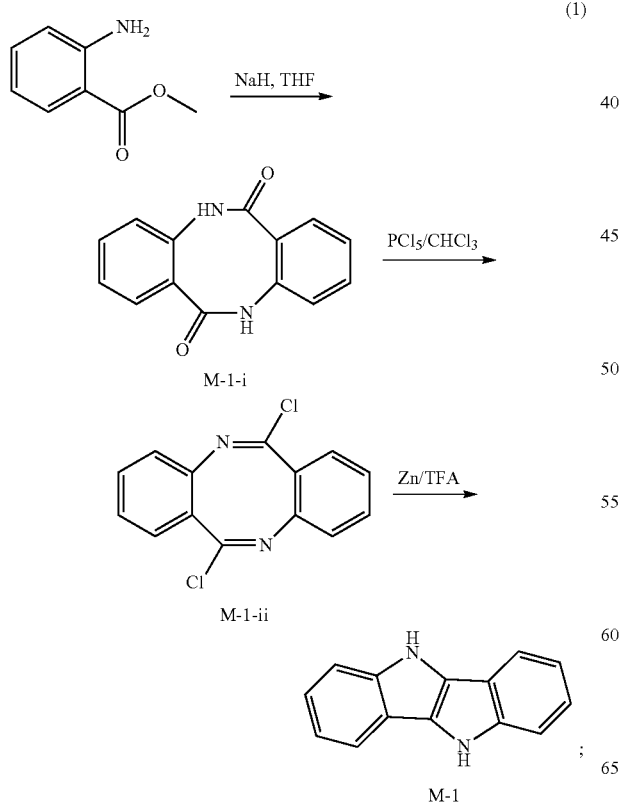

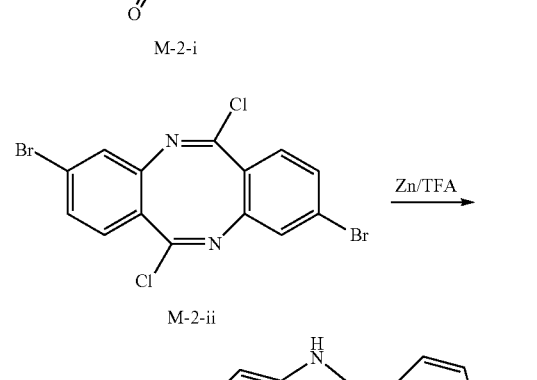

-continued (4)

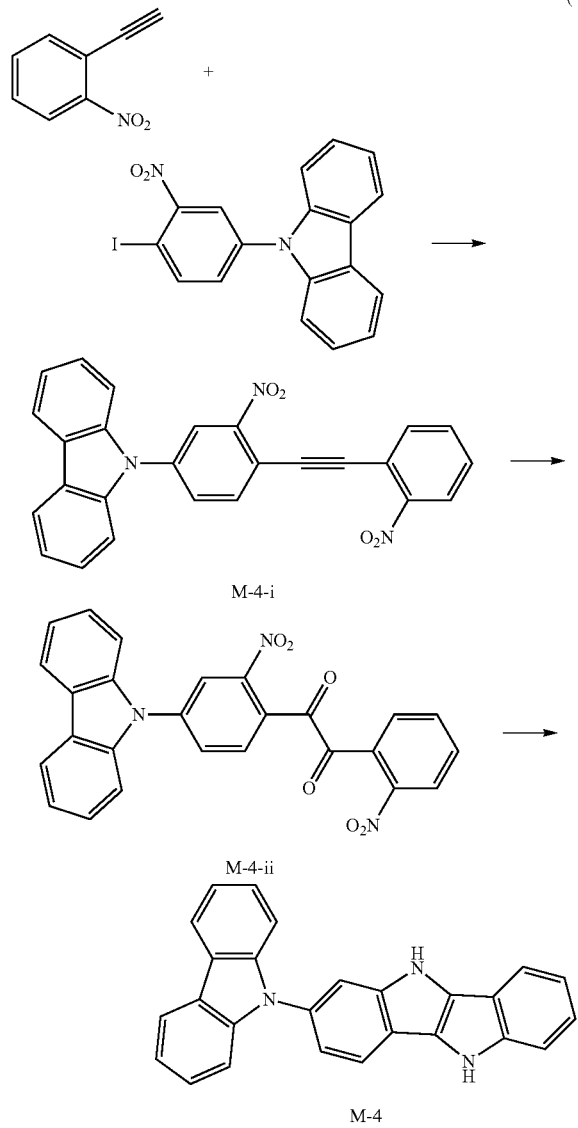

Examples of the present disclosure also provide an organic electroluminescent diode device comprising a cathode, an anode, and an organic functional layer formed between the cathode and the anode, wherein the organic functional layer comprises one or more light-emitting layers, wherein at least one of said light-emitting layers comprises a light-emitting material and a host material, and the host material comprises any of the compounds as described above.

Figure 2:
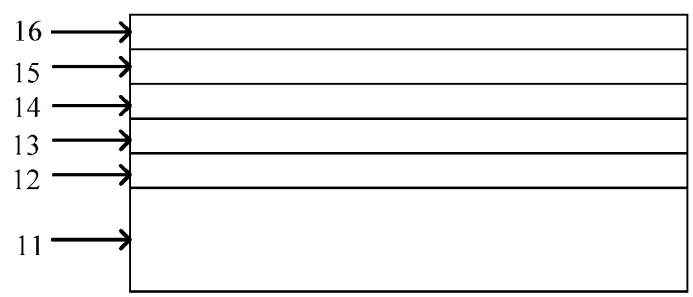
FIG. 2 is a schematic structural view of an OLED device provided in the example of the present disclosure.

An OLED device provided by one example of the present disclosure, as shown in FIG. 2, includes a substrate 11, an anode layer 12, a hole-transporting layer 13, a light-emitting layer 14, an electron-transporting layer 15 and a cathode layer 16. In another example, on the basis of the structure shown in FIG. 2, the OLED device may further include a hole injection layer located between the anode layer and the hole-transporting layer, or an electron injection layer located between the electron-transporting layer and the cathode layer. In another example, the cathode layer, the electron-transporting layer, the light-emitting layer, the hole-transporting layer and the anode layer may be sequentially formed on the substrate, i.e., the order of the functional layers on the substrate is reversed relative to the structure shown in FIG. 2.

The organic electroluminescent diode device in the present disclosure may be a phosphorescent device. Suitable phosphorescent dyes may be those known in the art, including complexes of heavy metals such as Ir, Pt, Os, Ru, Re and Pd, for example Ir complexes and Pt complexes, such as green dyes Ir(ppy)$_3$ and Ir(ppy)$_2$(acac), red dye PtOEP, blue phosphorescent dye FIrpic, and the like.

In examples of the present disclosure, the substrate may be a glass or plastic substrate.

The anode material may be a transparent, highly conductive material such as indium tin oxide (ITO), indium zinc oxide (IZO), tin dioxide (SnO$_2$), zinc oxide (ZnO), and the like.

Cathode can be made of metal and its mixture, such as Mg:Ag, Ca:Ag, etc., and alternatively be an electron injection layer/metal layer structure, such as LiF/Al, Li$_2$O.

EXAMPLES

The preparation, use and the like of the compounds of the present disclosure will be further described by way of specific examples. The starting materials and intermediates used in the present disclosure are commercially available unless otherwise specified.

Preparation of Intermediate Compound M-1

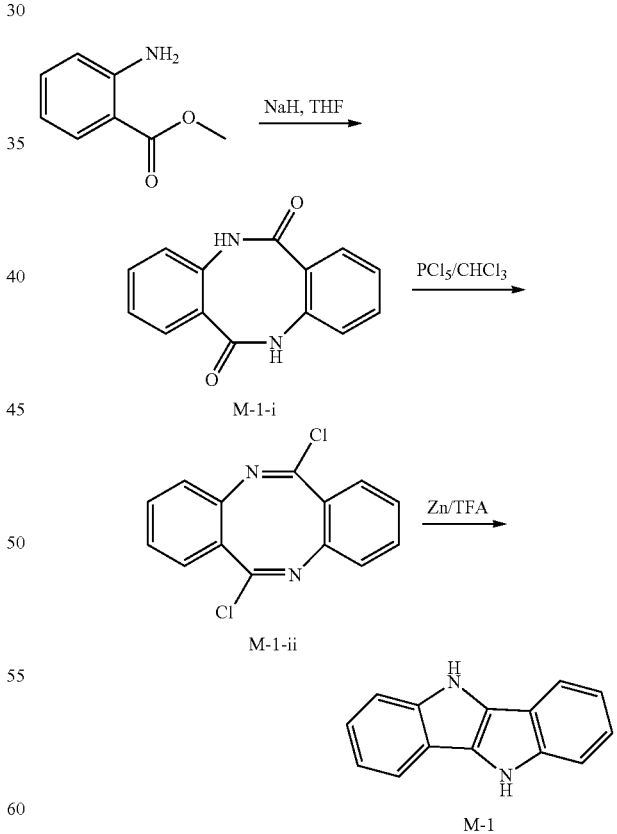

Preparation of compound M-1-i: NaH (14.0 g, 0.4 mol, 68%) and 180 mL anhydrous THF were added to a three-necked round bottomed flask under an inert atmosphere. 30.2 g (0.2 mol) of methyl 2-aminobenzoate dissolved in 150 mL of THF was slowly added dropwise at room temperature, and the mixture was heated under reflux for 3 days with magnetic stirring and then cooled to room temperature. The mixture was then slowly poured into 500 mL of 0.1 mol/L aqueous hydrochloric acid/ice. A large amount of precipitate occurred, and was filtered, washed and dried to give the crude product (compound M-1-i), which was purified by recrystallization to give 10.4 g of pale yellow crystals in 68.6% yield.

Preparation of compound M-1-ii: 9.5 g (0.04 mol) of compound M-1-i and 16.7 g (0.06 mol) of $PCl_5$ were mixed in 150 mL of chloroform, and refluxed for 3 hours and cooled to give the product (compound M-1-ii), which was purified by recrystallization to give 5.4 g of white crystals in 49.6% yield.

Preparation of intermediate compound M-1: 5.4 g (0.02 mol) of compound M-1-ii was dissolved in 100 mL of anhydrous THF and 9.6 g (0.15 mol) of activated Zn was added portionwise, followed by slow addition of 34 g (0.3 mol) of trifluoroacetic acid (TFA) with magnetic stirring, and the mixture was stirred at room temperature for 8 hours. The reaction was quenched by adding $NH_4Cl$ solution, and extracted with ethyl acetate. The organic phase was dried with anhydrous $MgSO_4$. The organic solvent was removed by rotary evaporation to give the crude product, which was recrystallized from ethanol to give 3.1 g of compound M-1 in 75.2% yield. Compound M-1: MS(m/z), 206; Elemental Analysis ($C_{14}H_{10}N_2$): Theoretical Value: C: 81.53%, H: 4.89%, N: 13.58%; Found: C: 81.44%, H: 4.80%, N: 13.51%.

Preparation of Intermediate Compound M-2

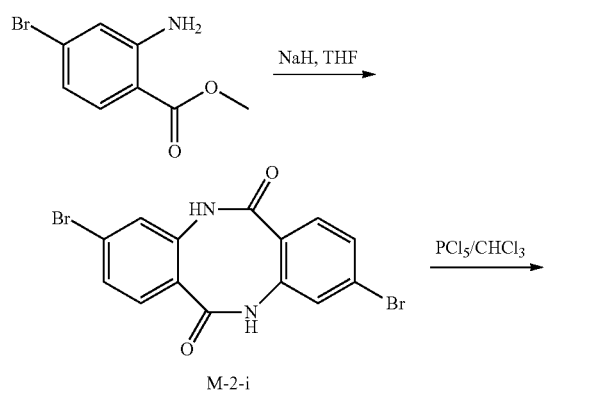

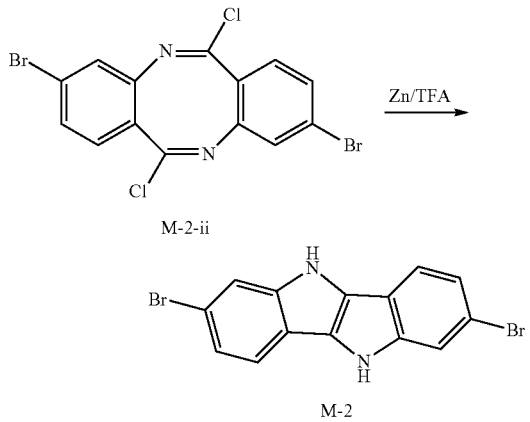

The intermediate compound M-2 was prepared using the same procedure as the intermediate compound M-1 except that methyl 2-aminobenzoate was replaced with methyl 4-bromo-2-aminobenzoate.

Preparation of Intermediate Compound M-3

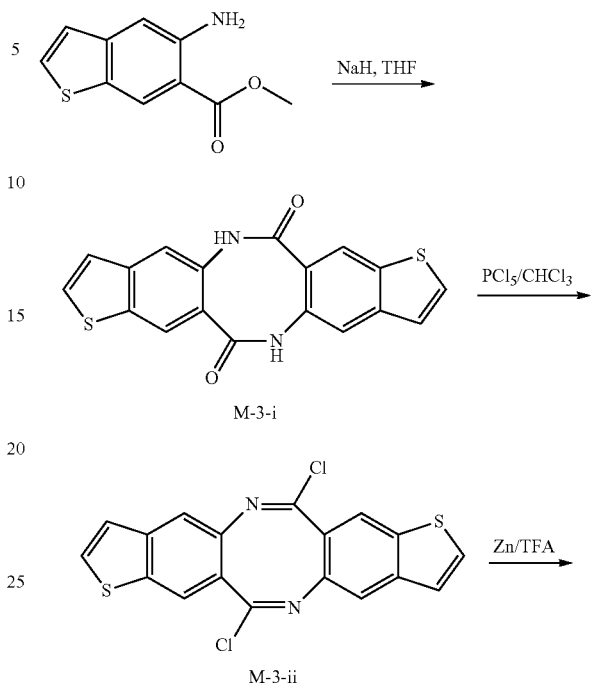

The intermediate compound M-3 was prepared using the same procedure as the intermediate compound M-1 except that methyl 2-aminobenzoate was replaced with methyl 5-aminobenzo[b]thiophene-6-carboxylate.

Preparation of Intermediate Compound M-4

The intermediate compound M-4 was prepared by the method shown below.

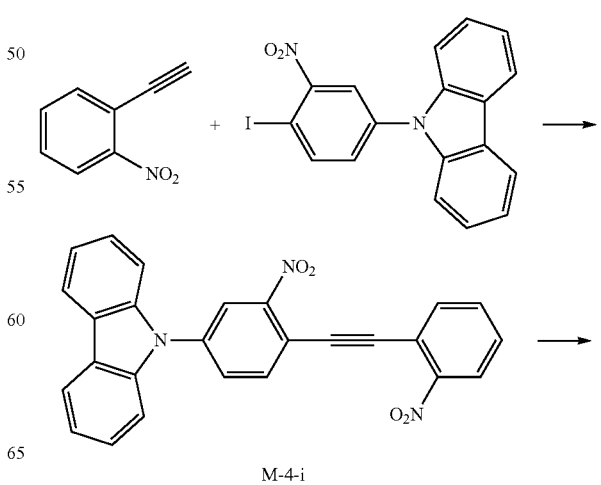

15

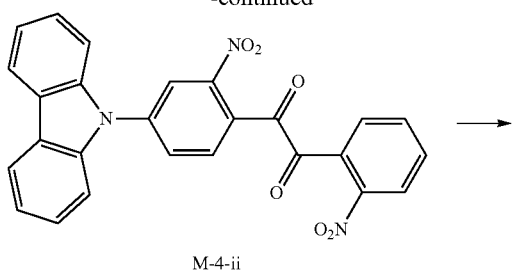

M-4-ii

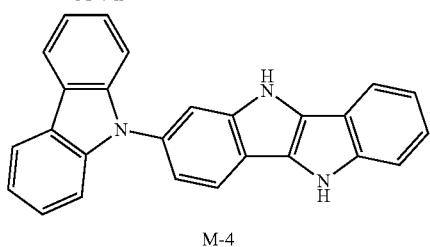

M-4

Preparation of compound M-4-i: To a three-necked round bottom flask were added 1-ethynyl-2-nitrobenzene (7.35 g, 0.05 mol), 9-(4-iodo-3-nitrophenyl)-9H-carbazole (20.7 g, 0.05 mol), triethylamine (600 mL), Pd(PPh$_3$)$_2$Cl$_2$ (1.42 g, 0.0021 mol), and CuI (0.285 g, 0.001 mol). The mixture was stirred at room temperature for 24 h. The precipitate occurred, and was filtered, washed, purified by column chromatography and then purified by recrystallization to give 17.9 g of a solid product in 82.6% yield.

Preparation of compound M-4-ii: The resulting compound M-4-i (17.3 g, 0.04 mol) was mixed with KMnO$_4$ (18.9 g, 0.12 mol), methyl trialkylammonium chloride (10 mL), CH$_2$Cl$_2$ (800 mL), water (500 mL), and acetic acid (50 mL). The mixture was stirred at 80° C. for 4 h and then extracted with CH$_2$Cl$_2$. The organic phase was dried over anhydrous MgSO$_4$. The organic solvent was removed by rotary evaporation to give the crude product which was purified by column chromatography to give 9.31 g of a solid product in 50% yield.

Preparation of intermediate compound M-4: The resulting compound M-4-ii (9.31 g, 0.02 mol) was mixed with SnCl$_2$.H$_2$O (67.5 g, 0.3 mol), acetic acid (1000 mL), and HCl (1.0 mol/L, 200 mL), and then stirred at 80° C. for 24 h. After distillation under reduced pressure, the mixture was dissolved in THF and ethyl acetate and washed with NaHCO$_3$ solution. After separation, the organic phase was dried over anhydrous MgSO$_4$ and the organic solvent was removed by rotary evaporation to give the crude product which was recrystallized from methanol to give 2.3 g of a white solid product in 31% yield. Compound M-4 MS(m/z): 206; Elemental Analysis (C$_{26}$H$_{17}$N$_3$): Theoretical Value: C: 84.07%, H: 4.61%, N: 11.31%; Found: C: 83.88%, H: 4.710%, N: 11.25%.

Example 1

Preparation of Compound C-1

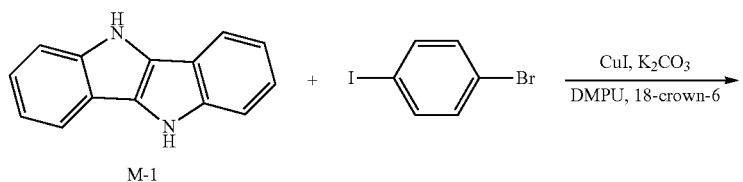

M-1

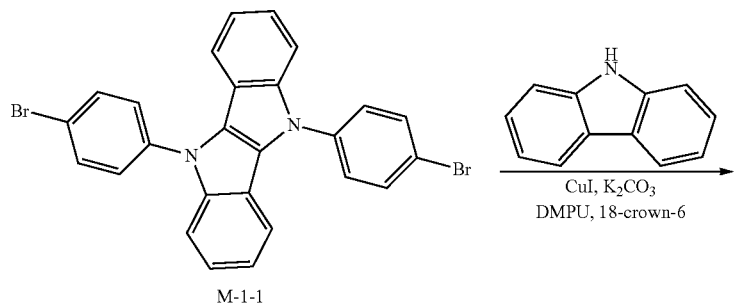

M-1-1

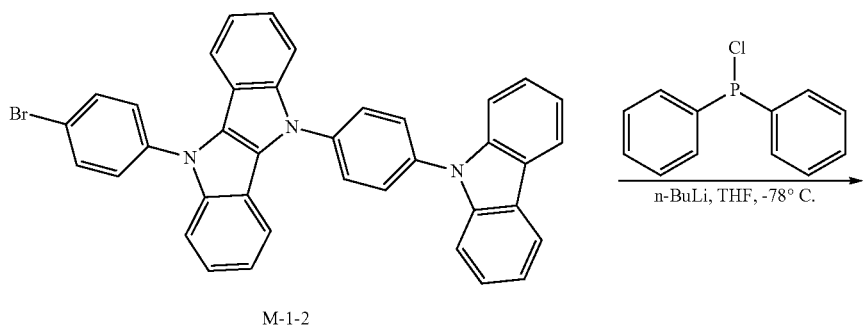

M-1-2

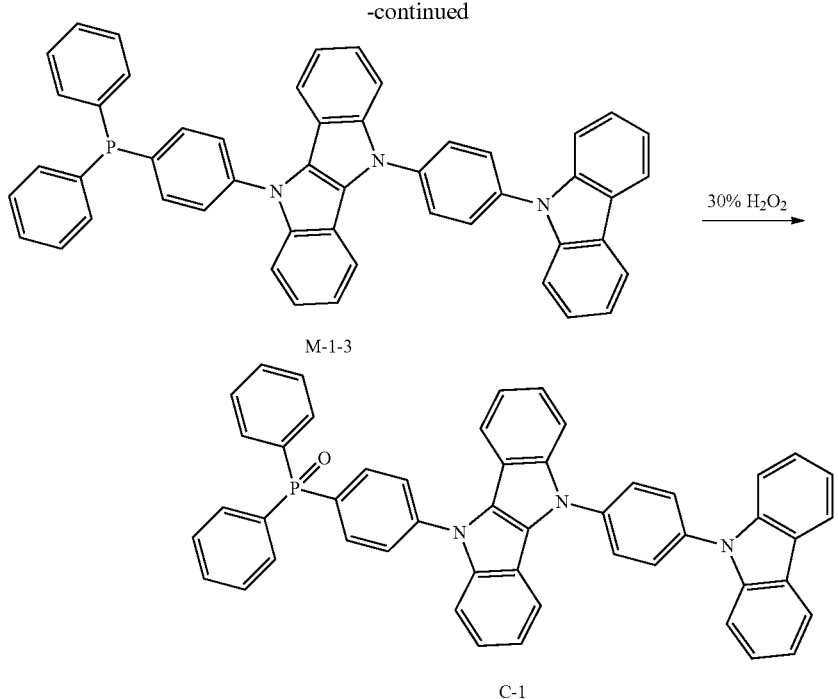

M-1-3

30% H₂O₂ →

C-1

Synthesis of compound M-1-1: This step was carried out using a Ullmann condensation reaction, which was in an inert atmosphere throughout the reaction. To a round bottom flask were added 10.3 g (0.05 mol) of M-1, 33.8 g (0.12 mol) of 4-bromoiodobenzene, 0.2 g (2 mol %) of CuI, 20.7 g (0.15 mol) of K₂CO₃, 0.8 g (6 mol %) of 18-crown-6, 5 mL of 1,3-dimethylpropyleneurea (DMPU) and 50 mL of o-dichlorobenzene. The reaction was refluxed under magnetic stirring for 18 h, then cooled, dissolved in CH₂Cl₂ and washed with water. The organic phase was dried and the organic solvent was removed by rotary evaporation to give the crude product (compound M-1-1), which was separated by silica gel column chromatography to give 20.1 g of solid in about 78.3% yield.

Synthesis of compound M-1-2: This step was carried out using the method described above, except that 4-bromoiodobenzene was replaced with carbazole and the reaction molar ratio of M-1-1:carbazole was controlled within 1:1.2. The reaction time was about 10 h, and finally the compound M-1-2 was obtained by separation.

Synthesis of compound M-1-3: Similarly, the synthesis process was carried out in an inert atmosphere. To a 500 ml three-necked round bottom flask, 12.0 g (0.02 mol) of compound M-1-2 and 200 ml of anhydrous THF were added. After the mixed liquid was cooled to about −78° C., 10 ml of n-BuLi solution (2.0 mol·L$^{-1}$, 0.025 mol) in n-hexane was slowly added dropwise under magnetic stirring. After the addition was complete, the reaction was stirred for 40 min, and then 5.5 g (0.025 mol) of diphenylphosphine chloride was added. After maintaining the reaction at this temperature for 2 h, the reaction solution was allowed to warm to room temperature and quenched by addition of ethanol. The organic solvent was removed to give a crude product. The crude product was washed several times with an appropriate amount of methanol and water, respectively, and then was separated by silica gel column chromatography to give 9.9 g of the product (compound M-1-3) in a yield of 70.1%.

Preparation of compound C-1: 7.1 g (0.01 mol) of compound M-1-3 was weighed and dissolved in 200 ml of CH₂Cl₂. 20 ml of H₂O₂ (W/W concentration was 30%) was added and stirred at room temperature for 12 h. The organic phase was then separated and the organic solvent was removed to give the crude product (compound C-1). The crude product was separated by silica gel column chromatography to give 6.4 g of white crystals in 88.6% yield.

Compound C-1 MS(m/z): 723; Elemental Analysis (C₅₀H₃₄N₃OP): Theoretical Value: C: 82.97%, H: 4.73%, N: 5.81%; Found: C: 82.79%, H: 4.62%, N: 5.76%. The energy level of compound C-1 was determined by cyclic voltammetry, HOMO: −6.01 eV, LUMO: −2.76 eV.

Example 2

Preparation of Compound C-4

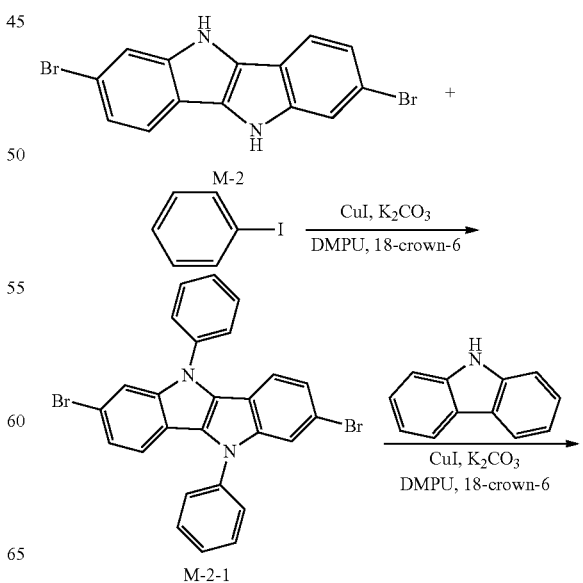

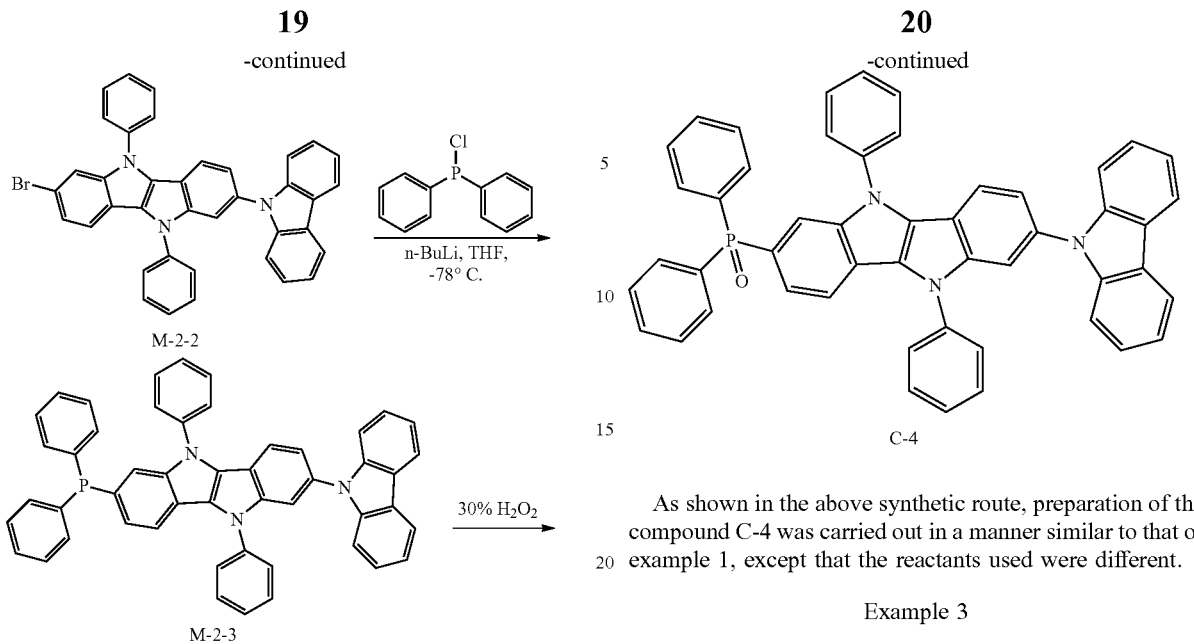
As shown in the above synthetic route, preparation of the compound C-4 was carried out in a manner similar to that of example 1, except that the reactants used were different.
Example 3
Preparation of Compound C-5
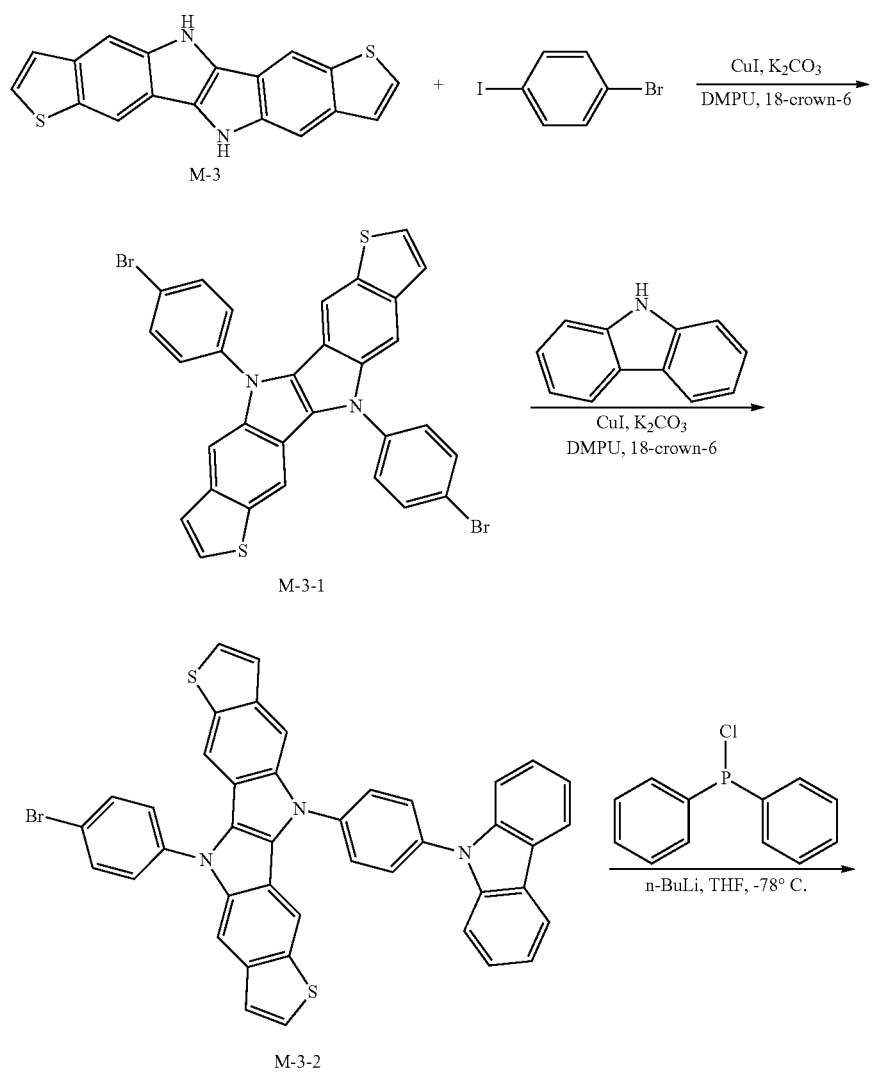

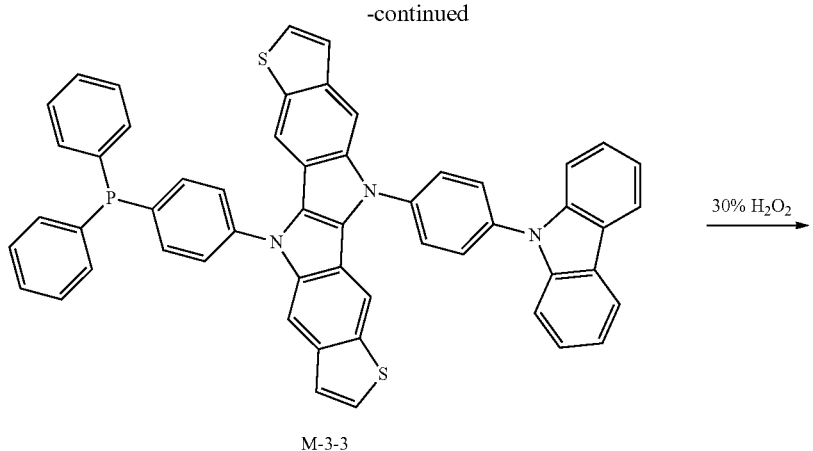
M-3-3
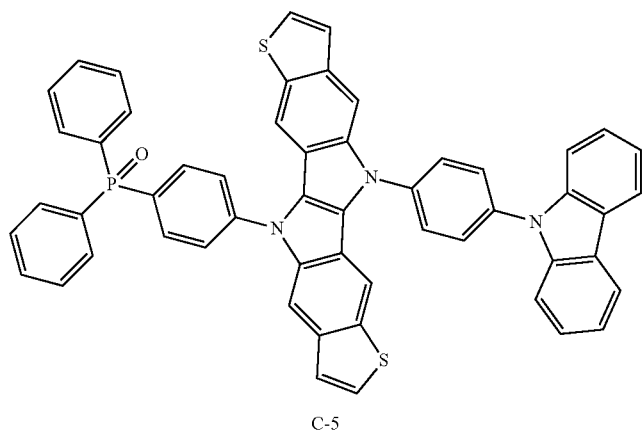
C-5
As shown in the above synthetic route, preparation of the compound C-5 was carried out in a manner similar to that of example 1 except that the reactants used were different.
Example 4
Preparation of Compound C-6
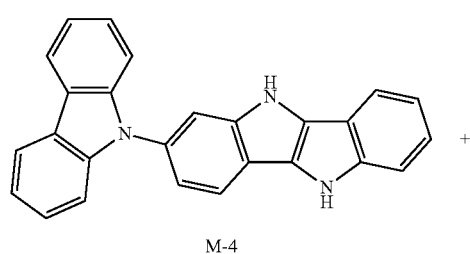
M-4
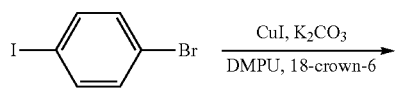
-continued
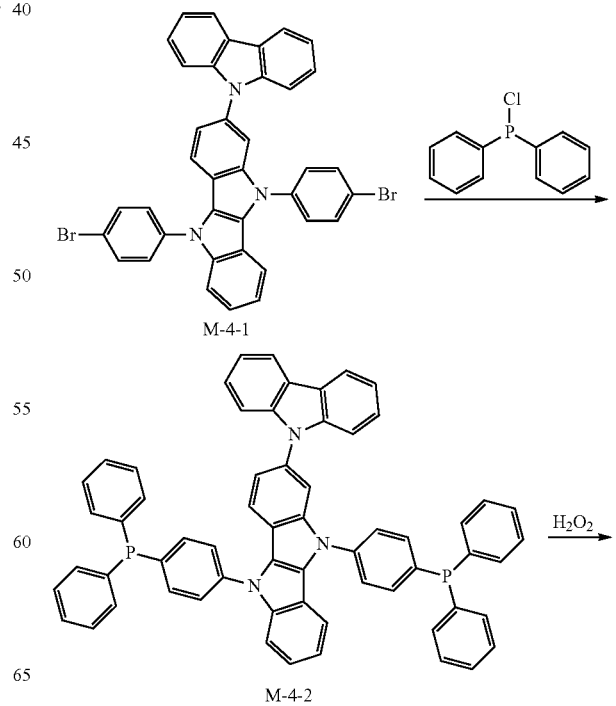
M-4-1
M-4-2

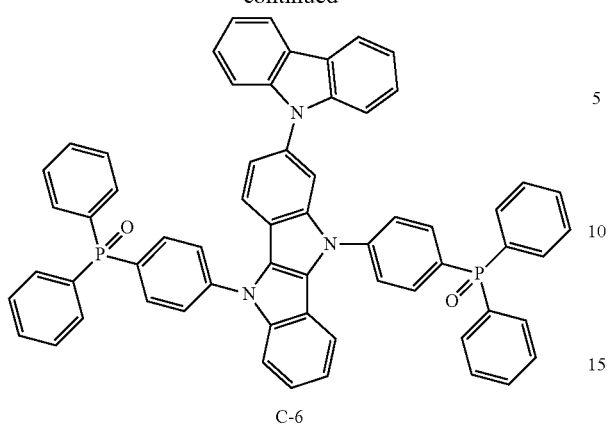
C-6
As shown in the above synthetic route, preparation of the compound C-6 was carried out in a manner similar to that of example 1, except that the reactants used were different. In addition, in the synthesis of M-4-2, the molar ratio of the reactants (M-4-1:diphenylphosphine chloride) was controlled as about 1:2.2.
Example 5
Preparation of Compound C-16
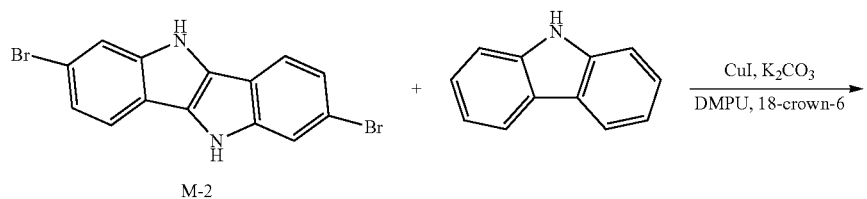
M-2
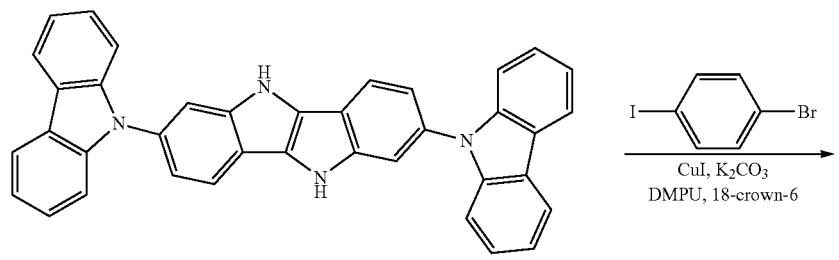
M-2-4
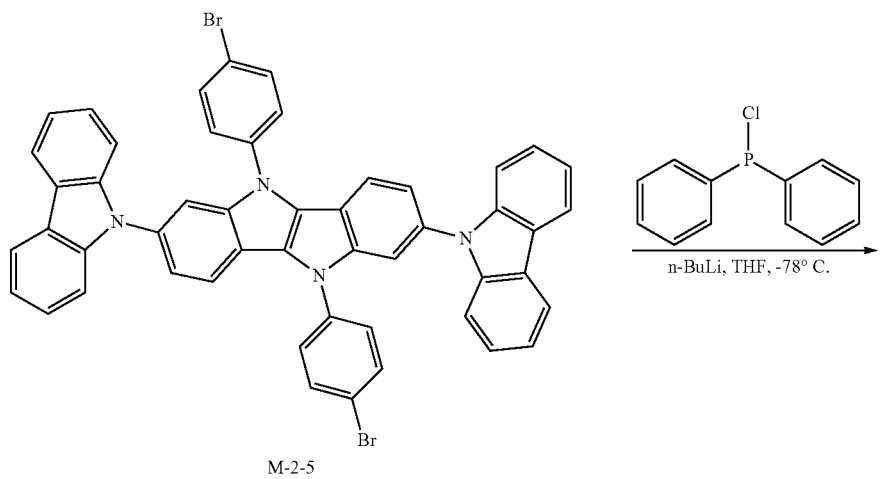
M-2-5

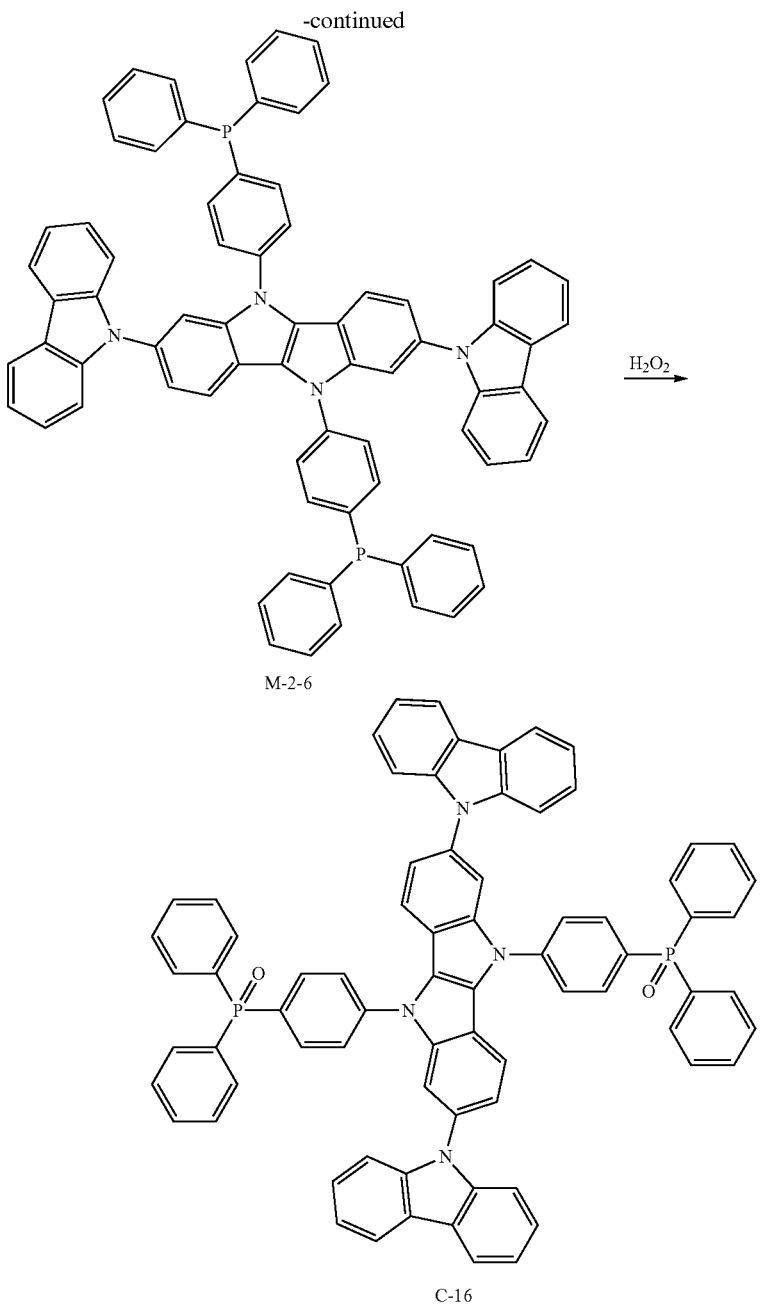

As shown in the above synthetic route, preparation of the compound C-16 is carried out in a manner similar to that of example 1, except that the reactants used were different. In addition, in the synthesis of M-2-4 and M-2-6, the molar ratio of the reactants (M-2:carbazole, and M-2-5:diphenylphosphine chloride) was controlled as about 1:2.2.

According to examples of the present disclosure, other compounds can also be synthesized. These compounds were prepared in a manner similar to those described above, and thus not described repeatedly. The analysis and energy level results of all the compounds (compound C-1 to C-16) synthesized above are listed in Table 1 below.

TABLE 1

| Compound No. | MS (m/z) of product | Molecular formula and MW | H$^1$-NMR (CDCl$_3$, 300 MHz) | HOMO (eV) | LUMO (eV) |
|---|---|---|---|---|---|
| C-1 | 723 | C$_{50}$H$_{34}$N$_3$OP 723.8 | δ = 8.74 (2H, t), 8.55(1H, m), 8.12(1H, m), 7.94(3H, m), 7.77(6H, m), 7.62(7H, m), 7.45(7H, m), 7.33(7H, m) | −6.01 | −2.76 |

TABLE 1-continued

| Compound No. | MS (m/z) of product | Molecular formula and MW | H¹-NMR (CDCl₃, 300 MHz) | HOMO (eV) | LUMO (eV) |
|---|---|---|---|---|---|
| C-2 | 723 | $C_{50}H_{34}N_3OP$ 723.8 | δ = 8.74(2H, t), 8.55(1H, m), 8.12(1H, m), 7.94(3H, m), 7.76(6H, m), 7.63(1H, m), 7.45(14H, m), 7.33(7H, m) | −5.86 | −2.59 |
| C-3 | 723 | $C_{50}H_{34}N_3OP$ 723.8 | δ = 8.74(2H, t), 8.55(1H, m), 7.94(4H, m), 7.77(6H, m), 7.45(7H, m), 7.62(3H, m), 7.50(2H, m), 7.58(2H, m), 7.33(4H, m), 7.25(2H, m) | −5.86 | −2.73 |
| C-4 | 723 | $C_{50}H_{34}N_3OP$ 723.8 | δ = 8.43(2H, t), 8.55(1H, t), 8.12(1H, m)7.94(1H, m), 7.76(4H, m), 7.83(2H, m), 7.43~7.63(20H, m), 7.25~7.33(3H, m) | −5.88 | −2.77 |
| C-5 | 835 | $C_{54}H_{34}N_3OPS_2$ 836.0 | δ = 8.55(1H, t), 8.12(1H, m)7.94(1H, m), 7.86(2H, m), 7.7(10H, m), 7.62(9H, m), 7.45(6H, m), 7.50(1H, m),7.25~7.33(3H, m) | −5.79 | −2.65 |
| C-6 | 923 | $C_{62}H_{43}N_3O_2P_2$ 924.0 | δ = 8.74(1H, m), 8.55(1H, m), 8.43(1H, t), 8.12(1H, m), 7.94(2H, m), 7.77(12H, m), 7.83(1H, m), 7.62(5H, m), 7.45~7.54(14H, m), 7.25~7.33(5H, m) | −6.05 | −2.80 |
| C-7 | 888 | $C_{62}H_{41}N_4OP$ 889.0 | δ = 8.74(1H, m), 8.55(2H, t), 8.43(1H, t), 8.12(2H, m), 7.94(3H, t), 7.77(4H, m), 7.83(1H, s), 7.62(10H, m), 7.43~7.50(9H, m), 7.25~7.33(8H, m) | −6.12 | −2.79 |
| C-8 | 875 | $C_{62}H_{42}N_3OP$ 876.0 | δ = 8.55(1H, t), 8.49(2H, t), 8.10(3H, m), 7.94(1H, t), 7.77(6H, t), 7.63(9H, m), 7.25~7.52(20H, m) | −5.99 | −2.58 |
| C-9 | 953 | $C_{66}H_{44}N_5OP$ 954.1 | δ = 8.55(1H, t), 8.12(1H, t), 7.94(1H, t), 7.76(6H, t), 7.63(9H, m), 7.25~7.62(33H, m), 6.52(2H, t) | −6.00 | −2.67 |
| C-10 | 835 | $C_{58}H_{50}N_3OP$ 836.0 | δ = 8.55(2H, t), 8.35(2H, t), 8.12(1H, m), 7.94(6H, m), 7.77(6H, t), 7.62(6H, m), 7.45(6H, m), 7.50(1H, m), 7.30(3H, m), 7.03(2H, t), 1.35(18H, s) | −6.09 | −2.73 |
| C-11 | 877 | $C_{60}H_{40}N_5OP$ 878.0 | δ = 8.55(1H, t), 8.43(2H, t), 8.30(4H, m), 8.12(1H, t), 7.94(1H, t), 7.77(4H, t), 7.83(2H, s), 7.25~7.50(24H, t) | −6.21 | −2.91 |
| C-12 | 827 | $C_{54}H_{34}N_7OP$ 827.9 | δ = 8.74(4H, s), 8.65(1H, t), 8.07(4H, s), 8.12(1H, t), 7.94(1H, t), 7.77(6H, t), 7.62(7H, s), 7.45(6H, m), 7.50(1H, m), 7.29~7.33(3H, m) | −5.79 | −2.65 |
| C-13 | 1027 | $C_{74}H_{50}N_3OP$ 1028.2 | δ = 8.55(1H, t), 8.43(2H, t), 8.12(1H, t), 8.05(4H, s), 7.94(1H, t), 7.88(2H, m), 7.77(4H, m), 7.83(2H, m), 7.63(1H, m), 7.29~7.51(32H, m) | −5.81 | −2.66 |
| C-14 | 1033 | $C_{68}H_{44}N_9OP$ 1034.1 | δ = 8.55(1H, t), 8.43(2H, t), 8.28(8H, m), 8.12(1H, t), 7.94(1H, t), 7.77(4H, m), 7.83(2H, m), 7.63(1H, t), 7.25~7.51(24H, m) | −5.93 | −2.76 |
| C-15 | 923 | $C_{66}H_{42}N_3OP$ 924.0 | δ = 8.90(4H, t), 8.55(1H, t), 8.43(2H, t), 8.10(4H, t), 8.12(1H, t), 7.77~7.90(16H, t), 7.94(1H, m), 7.45~7.54(9H, m), 7.25~7.33(3H, m) | −6.00 | −2.81 |

TABLE 1-continued

| Compound No. | MS (m/z) of product | Molecular formula and MW | H¹-NMR (CDCl₃, 300 MHz) | HOMO (eV) | LUMO (eV) |
|---|---|---|---|---|---|
| C-16 | 1088 | $C_{74}H_{50}N_4O_2P_2$ 1089.2 | δ = 8.55(2H, t), 8.43(2H, t), 8.12(2H, t), 7.94(2H, t), 7.77(12H, m), 7.83(2H, s), 7.62(6H, m), 7.45(12H, m), 7.50(2H, m), 7.54(2H, m), 7.29~7.35(6H, m) | −5.88 | −2.72 |

Example 6

Composition Example

A method of preparing an organic electroluminescent composition for a light-emitting layer comprises mixing a host material with a light-emitting material.

In this example, the host material used any one or more of C-1 to C-16, and the light-emitting material used a blue phosphorescent dye Firpic, wherein the host material accounted for 94 wt % of the total composition, and the light-emitting material accounted for 6 wt % of the total composition.

Example 7

The OLED device was fabricated using the organic electroluminescent compositions of the present disclosure. The structure of the OLED device in this example was: substrate/anode (ITO)/hole-transporting layer (HTL)/organic light-emitting layer (EL)/electron-transporting layer (ETL)/electron injection layer (EIL)/cathode (metal electrode).

The materials used in this example had the following formulas:

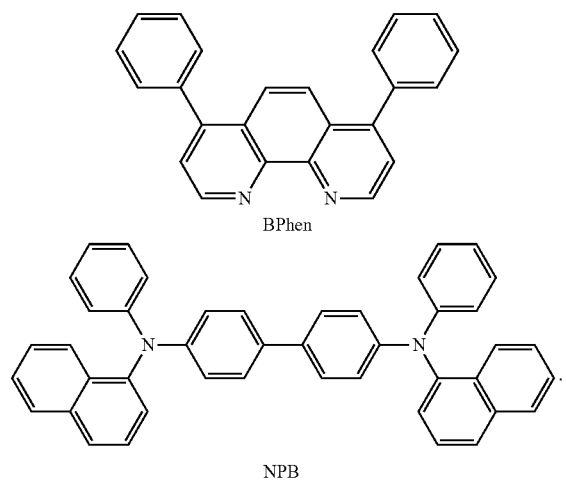

BPhen

NPB

In the device fabrication of the present example, a glass substrate was used as a substrate, and ITO (indium tin oxide) was selected as the anode material.

In the device fabrication of the present example, NPB (i.e., N,N'-bis (naphthalen-2-yl)-N,N'-bis(phenyl)biphenyl-4,4'-diamine) was selected as the hole-transporting material.

In the device fabrication of the present example, LiF was selected as the electron injection material, and Al was the cathode material.

The specific preparation process was as follows:

A hole-transporting material NPB having a thickness of 35 nm and a light-emitting layer (a composition obtained from example 6) were successively deposited by vacuum evaporation on a cleaned glass substrate covered with a transparent electrode ITO. 25 nm Bphen was then deposited as an electron-transporting layer of the device. On the electron-transporting layer, by vacuum evaporation, 0.5 nm LiF was deposited as an electron injection layer and an Al layer having the thickness of 100 nm was deposited as a cathode of the device.

The OLED device was prepared according to the process described in the present example, which used compound C-1 as the host material of the light-emitting layer, and had the following structure:

ITO/NPB(35 nm)/compound C-1:6% Firpic (30 nm)/Bphen(25 nm)/LiF(0.5 nm)/Al(100 nm).

Example 8

The OLED device was prepared as described in Example 7, except that compound C-8 was used as the host material of the light-emitting layer. It had the following structure:
ITO/NPB(35 nm)/compound C-8:6% Firpic (30 nm)/Bphen(25 nm)/LiF(0.5 nm)/Al(100 nm).

Example 9

The OLED device was prepared as described in Example 7, except that compound C-16 was used as the host material of the light-emitting layer. It had the following structure:
ITO/NPB(35 nm)/compound C-16:6% Firpic (30 nm)/Bphen(25 nm)/LiF(0.5 nm)/Al(100 nm).

Comparative Example 1

The OLED device was prepared as described in Example 7, except that compound CBP was used as the host material of the light-emitting layer. It had the following structure:
ITO/NPB(35 nm)/CBP: 6% Firpic (30 nm)/Bphen(25 nm)/LiF(0.5 nm)/Al(100 nm).

In this structure, the light-emitting layer used 94 wt % of CBP (4,4-N,N-dicarbazolyl biphenyl) and 6 wt % of blue phosphorescent dye Firpic.

The energy levels of the devices of Comparative Example 1 and Example 7 were shown in FIG. 1. The properties of the devices of Comparative Example 1 and Examples 7-9 were tested, and their results were shown in the following table.

TABLE 2

| Devices | Luminance cd/m² | Voltage V | Current Efficiency cd/A | Color |
|---|---|---|---|---|
| Comparative Example 1 | 1000 | 3.46 | 5.98 | blue |
| Example 7 | 1000 | 3.22 | 6.68 | blue |

TABLE 2-continued

| Devices | Luminance cd/m$^2$ | Voltage V | Current Efficiency cd/A | Color |
|---|---|---|---|---|
| Example 8 | 1000 | 3.09 | 6.23 | blue |
| Example 9 | 1000 | 3.16 | 6.84 | blue |

According to the results of the above table, the organic electroluminescent host materials of the present disclosure have excellent properties compared to conventional materials: the driving voltage of the organic electroluminescent device can be reduced, the current efficiency can be increased, and thus the power consumption of the OLED in illumination and display can be reduced.

The foregoing is merely illustrative of the present invention and is not intended to limit the scope of the invention, and the scope of the invention is defined by the appended claims.

This application claims the benefit of priority from Chinese Patent Application No. 201610236613.4, filed on Apr. 15, 2016, which is hereby incorporated by reference in its entirety as part of this application.

What is claimed is:

1. A compound of formula (1),

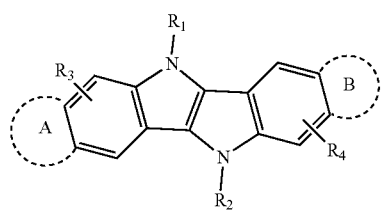

Formula (1)

wherein $R_1$, $R_2$, $R_3$ and $R_4$ are each independently selected from hydrogen, a substituted or unsubstituted $C_{1-20}$ alkyl, a substituted or unsubstituted $C_{3-20}$ cycloalkyl, a substituted or unsubstituted aromatic hydrocarbyl, or a substituted or unsubstituted aromatic heterocyclic group; and at least one of $R_1$, $R_2$, $R_3$ and $R_4$ contains a group having a hole-transporting ability; and at least one of $R_1$, $R_2$, $R_3$ and $R_4$ contains a group having an electron-transporting ability;

A and B each independently represent hydrogen, a substituted or unsubstituted, fused aromatic ring, or a substituted or unsubstituted, fused heteroaromatic ring containing a heteroatom(s) selected from O, N and S;

the group having an electron-transporting ability is a substituted or unsubstituted diphenylphosphine oxide group;

the group having a hole-transporting ability is selected from groups derived from aromatic triamines, carbazoles, organosilicons, and organometallic complexes.

2. The compound according to claim 1, wherein the aromatic hydrocarbyl is selected from the group consisting of phenyl, biphenylyl, naphthyl, phenanthryl, naphthylphenyl and fluorenyl, which are substituted or unsubstituted.

3. The compound according to claim 1, wherein the aromatic heterocyclic group is selected from the group consisting of pyridyl, imidazolyl, carbazolyl and benzimidazolyl, which are substituted or unsubstituted.

4. The compound according to claim 1, wherein the substituents at each occurrence are independently selected from $C_1$-$C_{10}$ alkyl, $C_1$-$C_{10}$ alkoxyl, $C_3$-$C_{20}$ cycloalkyl, $C_6$-$C_{20}$ aryl or $C_4$-$C_{20}$ heteroaryl.

5. The compound according to claim 1, wherein the group having a hole-transporting ability is a substituted or unsubstituted carbazole group.

6. The compound according to claim 1, wherein a π-π conjugation is formed between the group having a hole-transporting ability and the indolo[3,2-b]indole main aromatic structure in the compound of formula (1); and a π-π conjugation is formed between the group having an electron-transporting ability and the indolo[3,2-b]indole main aromatic structure.

7. The compound according to claim 1, wherein the compound has at least one of the following structural formulas:

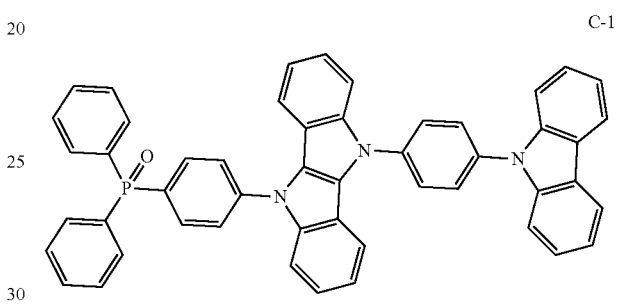

C-1

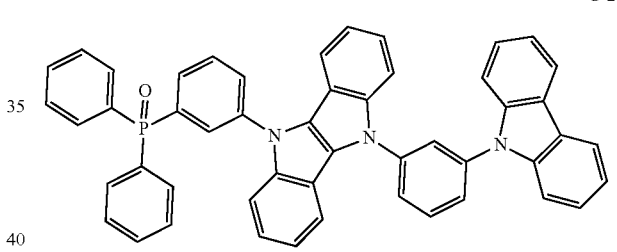

C-2

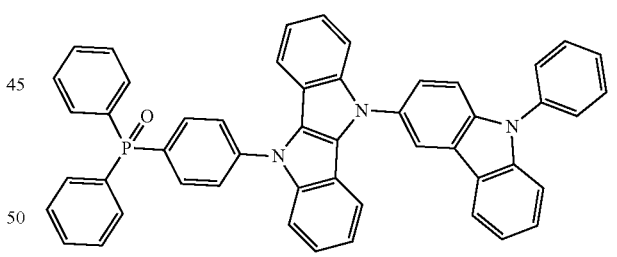

C-3

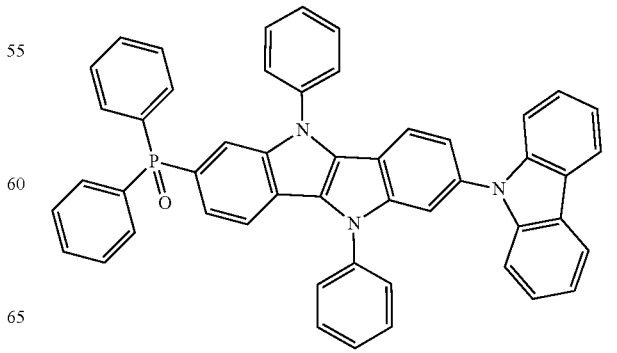

C-4

-continued
C-5
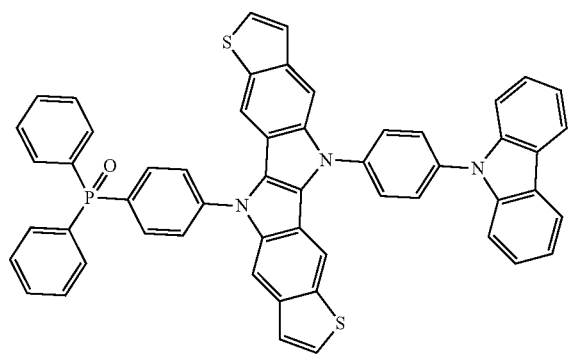
C-6
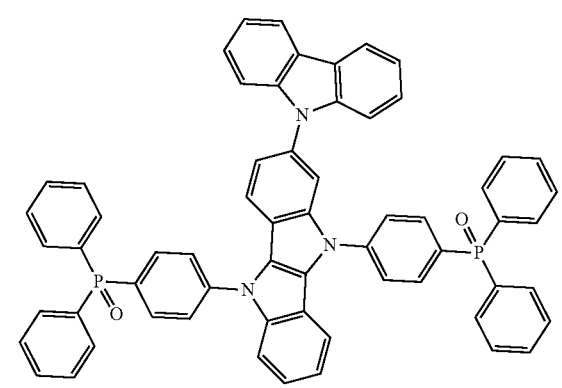
C-7
C-8
-continued
C-9
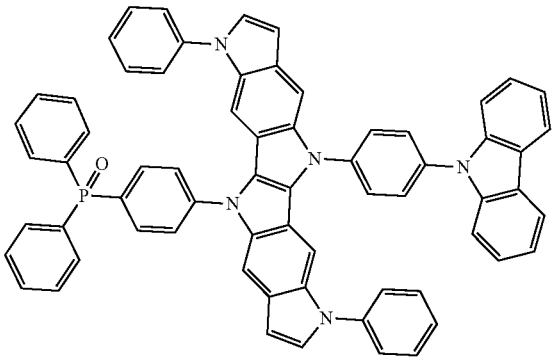
C-10
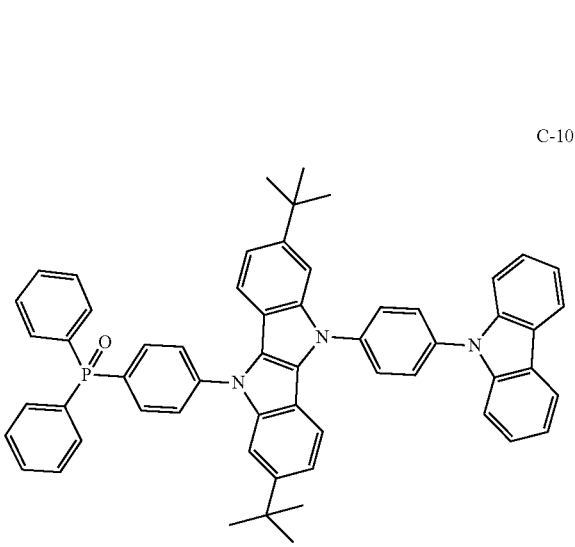
C-11
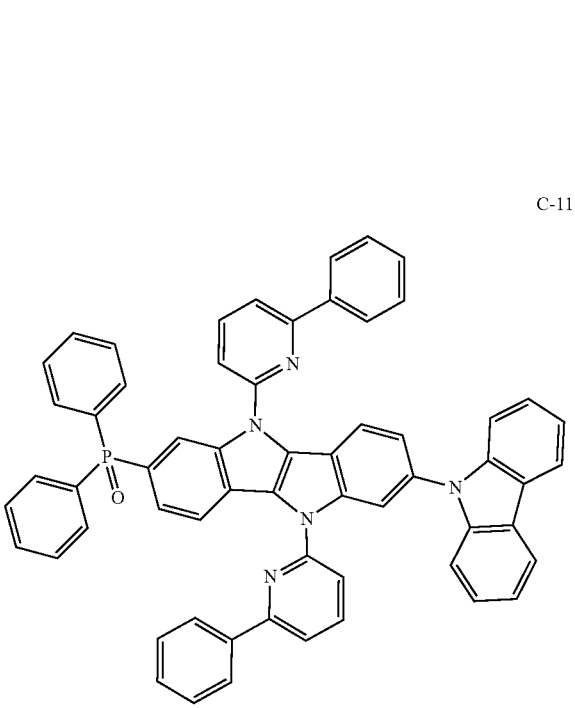

C-12

C-13

C-14

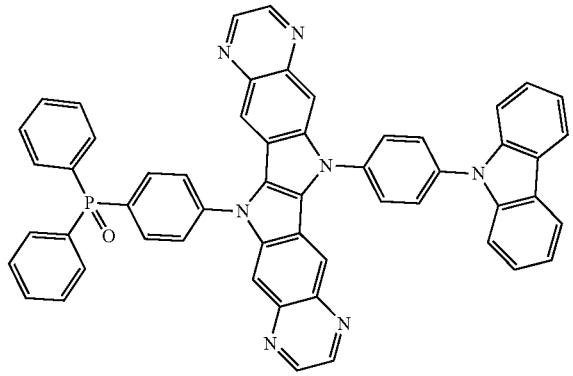

C-15 and

C-16

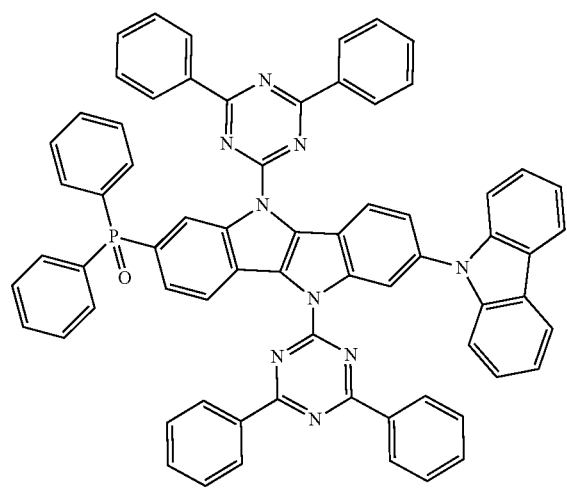

8. An organic electroluminescent composition comprising a light-emitting material and a host material, wherein the host material comprises the compound according to claim 1.

9. The composition according to claim 8, wherein the light-emitting material comprises at least one selected from the group consisting of a fluorescent light-emitting material and a phosphorescent light-emitting material.

10. The composition according to claim 9, wherein the phosphorescent light-emitting material comprises at least one of Ir complexes, Pt complexes, Os complexes, Ru complexes, Re complexes, and Pd complexes.

11. The composition according to claim 8, wherein the host material accounts for 80 to 98 wt % of the composition.

12. The composition according to claim 8, wherein the host material accounts for 90 to 95 wt % of the composition.

13. An organic electroluminescent diode device, comprising a cathode, an anode, and an organic functional layer formed between the cathode and the anode, wherein:
the organic functional layer comprises one or more light-emitting layers, and at least one of the light-emitting layers comprises a light-emitting material and a host material, and the host material comprises the compound according to claim 1.

\* \* \* \* \*